US011948694B2

(12) United States Patent
Gopalakrishnan et al.

(10) Patent No.: US 11,948,694 B2
(45) Date of Patent: Apr. 2, 2024

(54) CONTROLLING COMPARTMENTAL FLOWS IN EPIDEMIOLOGICAL MODELING BASED ON MOBILITY DATA

(71) Applicant: Merative US L.P., Ann Arbor, MI (US)

(72) Inventors: Vishrawas Gopalakrishnan, Cambridge, MA (US); Sayali Navalekar, Westford, MA (US); James H. Kaufman, San Jose, CA (US); Simone Bianco, San Francisco, CA (US); Kun Hu, Santa Clara, CA (US); Ajay Ashok Deshpande, Pleasantville, NY (US); Sarah Kefayati, San Francisco, CA (US); Ujwal Reddy Moramganti, Ashburn, VA (US); George Sirbu, Saline, MI (US); Xuan Liu, Yorktown Heights, NY (US); Raman Srinivasan, Plano, TX (US); Pan Ding, New York, NY (US)

( * ) Notice: Subject to any disclaimer, the term of this patent is extended or adjusted under 35 U.S.C. 154(b) by 265 days.

(21) Appl. No.: 17/318,027

(22) Filed: May 12, 2021

(65) Prior Publication Data

US 2022/0367067 A1 Nov. 17, 2022

(51) Int. Cl.
*G06Q 30/00* (2023.01)
*G06N 20/00* (2019.01)
(Continued)

(52) U.S. Cl.
CPC .............. *G16H 50/80* (2018.01); *G06N 20/00* (2019.01); *G16H 50/50* (2018.01)

(58) Field of Classification Search
None
See application file for complete search history.

(56) References Cited

U.S. PATENT DOCUMENTS 8,234,129 B2 7/2012 Michon et al.
8,498,879 B2 7/2013 Michon et al.
(Continued)

FOREIGN PATENT DOCUMENTS

CN 106709252 A 5/2017
CN 111445997 A 7/2020
(Continued)

OTHER PUBLICATIONS

Chae, Sangwon et al., "Predicting Infectious Disease Using Deep Learning and Big Data", International Journal of Environmental Research and Public Health, 20 pages, Jul. 2018.
(Continued)

*Primary Examiner* — Matthew T Sittner
(74) *Attorney, Agent, or Firm* — Stephen J. Walder, Jr.

(57) ABSTRACT

Mechanisms are provided for compartmental epidemiological computer modeling based on mobility data. Machine learning training of an isolation rate prediction computer model is performed to generate a trained isolation rate prediction model that predicts an isolation rate of a biological population. Isolation data is received which comprises data indicating a measure of mobility of the biological population. The trained isolation rate prediction model is executed on input features extracted from the isolation data to generate a predicted isolation rate. A compartmental epidemiological computer model, comprising a plurality of compartments representing states of a population with regard to an infectious disease, is executed to simulate a progression of the infectious disease and flows of portions of the population from between compartments in the compartmental epidemiological computer model are controlled based on the predicted isolation rate.

20 Claims, 4 Drawing Sheets

(51) Int. Cl.
  *G16H 50/50* (2018.01)
  *G16H 50/80* (2018.01)

(56) References Cited

U.S. PATENT DOCUMENTS

| | | | |
|---|---|---|---|
| 10,444,235 | B2 | 10/2019 | Donovan et al. |
| 2003/0009239 | A1 | 1/2003 | Lombardo et al. |
| 2007/0229290 | A1 | 10/2007 | Kahn et al. |
| 2008/0208813 | A1 | 8/2008 | Friedlander et al. |
| 2010/0138160 | A1 | 6/2010 | Jacquez et al. |
| 2011/0093249 | A1 | 4/2011 | Holmes et al. |
| 2017/0103172 | A1 | 4/2017 | Fink et al. |
| 2017/0300657 | A1 | 10/2017 | Barrett et al. |
| 2017/0316324 | A1 | 11/2017 | Barrett et al. |
| 2018/0366221 | A1 | 12/2018 | Crehore et al. |
| 2019/0131018 | A1* | 5/2019 | Sones .............. G16H 50/80 |
| 2021/0050116 | A1 | 2/2021 | Sabeti et al. |
| 2022/0013241 | A1 | 1/2022 | Meyerson et al. |
| 2022/0033446 | A1* | 2/2022 | Burk ................ C07K 7/56 |
| 2022/0199266 | A1 | 6/2022 | Achin et al. |
| 2022/0280621 | A1* | 9/2022 | van Buuren .......... A61P 35/00 |

FOREIGN PATENT DOCUMENTS

| | | |
|---|---|---|
| CN | 111968751 A | 11/2020 |
| CN | 112163705 A | 1/2021 |

OTHER PUBLICATIONS

Dublin, Sascha et al., "Natural Language Processing to Identify Pneumonia from Radiology Reports", National Institute of Health, Author Manuscript, Pharmacoepidemiol Drug Saf, 15 pages, Aug. 2013.
Halder, Nilimesh et al., "Analysis of the Effectiveness of Interventions Used During the 2009 A/H1N1 Influenza Pandemic", BioMed Central Public Health Research Article 2010, 10:168, 14 pages, Oct. 2010.
Hogan, Larry et al., "Maryland Targeting Plan for Areas at Risk for Childhood Lead Poisoning", Maryland Department of Health and Mental Hygiene, 90 pages, Oct. 2015.
List of IBM Patents or Patent Applications Treated as Related, Jul. 29, 2021, 2 pages.
"2019 novel Corona Virus Model", Eclipse Foundation, https://wiki.eclipse.org/2019_novel_Corona_Virus_Model, last modified Sep. 20, 2020, Accessed Feb. 25, 2021, 23 pages.
Baek, Jackie et al., "The Limits to Learning an SIR Process: Granular Forecasting for Covid-19", https://arxiv.org/abs/2006.06373, Submitted on Jun. 11, 2020, 24 pages.
Gopalakrishnan, Vishrawas et al., Pending U.S. Appl. No. 17/332,219, filed May 27, 2021, titled "Hyperlocal Prediction of Epidemic Dynamics and Risks", 126 pages.
Gopalakrishnan, Vishrawas et al., Pending U.S. Appl. No. 17/332,356, filed May 27, 2021, titled "Hypothetical Scenario Evaluation in Infectious Disease Dynamics Based on Similar Regions", 125 pages.
Gopalakrishnan, Vishrawas et al., Pending U.S. Appl. No. 17/332,485, filed May 27, 2021, titled "Adapting Computer Modeling of Infectious Disease Based on Noisy Data", 125 pages.
Gopalakrishnan, Vishrawas et al., Pending U.S. Appl. No. 17/332,587, filed May 27, 2021, titled "Automatic Intervention Detection in Infectious Disease Case Reports", 124 pages.
Gopalakrishnan, Vishrawas et al., Pending U.S. Appl. No. 17/332,674, filed May 27, 2021, titled "Automated Monitoring and Retraining of Infectious Disease Computer Models", 126 pages.
Gopalakrishnan, Vishrawas et al., "Globally Local: Hyper-Local Modeling for Accurate Forecast of COVID-19", MedRxiv preprintdoi: https://www.medrxiv.org/content/10.1101/2020.11.16.20232686v1.full, posted Nov. 18, 2020, 31 pages.
Kefayati, Sarah et al., "On Machine Learning-Based Short-Term Adjustment of Epidemiological Projections of COVID-19 in US", medRxiv preprint doi: https://www.medrxiv.org/content/10.1101/2020.09.11.20180521v1, posted Sep. 13, 2020, 8 pages.
Prem, Kiesha et al., "The effect of control strategies to reduce social mixing on outcomes of the COVID-19 epidemic in Wuhan, China: a modelling study", www.thelancet.com/public-health, v. 5, n. 5, Lancet Public Health, e261-e270, Published Online Mar. 25, 2020, 10 pages.
Rodríguez, Alexander et al., "DeepCOVID: An Operational Deep Learning-driven Framework for Explainable Real-time COVID-19 Forecasting", medRxiv preprint doi: https://www.medrxiv.org/content/10.1101/2020.09.28.20203109v2, Dec. 24, 2020, 8 pages.
Srivastava, Ajitesh et al., "Fast and Accurate Forecasting of COVID-19 Deaths Using the SIkJα Model", https://arxiv.org/abs/2007.05180, Submitted on Jul. 10, 2020 (v1), last revised Jul. 13, 2020 (this version, v2), 12 pages.
Yang, Hyun M. et al., "Mathematical modeling of the transmission of SARS-COV-2—Evaluating the impact of isolation in São Paulo State (Brazil) and lockdown in Spain associated with protective measures on the epidemic of covid-19", medRxiv preprint doi: https://www.medrxiv.org/content/10.1101/2020.07.30.20165191v1, Posted Aug. 1, 2020, 54 pages.
Zou, Difan et al., "Epidemic Model Guided Machine Learning for COVID-19 Forecasts in the United States", medRxiv preprint doi: https://www.medrxiv.org/content/10.1101/2020.05.24.20111989v1, posted May 25, 2020, 15 pages.
Anonymous, "A System and a Method for Governing a Big Data-Centric Environment", IP.com Prior Art Database Technical Disclosure, IP.com No. IPCOM000241368D, Apr. 21, 2015, 6 pages.
Anonymous, "Machine Learning Algorithms for Smart Meter Diagnostics", IP.com Prior Art Database Technical Disclosure, IP.com No. IPCOM000242462D, Jul. 16, 2015, 53 pages.
Anonymous, "System and Method for Modeling and Controlling the Spread of Infectious Agents", IP.com Prior Art Database Technical Disclosure, IP.com No. IPCOM000264158D, Nov. 17, 2020, 9 pages.
Bird, Alexander, "A simple introduction to epidemiological modelling—the SIR model", King's College London, Peter Sowerby Philosophy & Medicine Project, 2020, 10 pages.
Dght, "Using Data to Drive Better Programs", U.S. Centers for Disease Control and Prevention (CDC), Division of Global HIV & TB, Dec. 2018, 2 pages.
Miller, Andrew C. et al., "Mobility trends provide a leading indicator of changes in SARS-COV-2 transmission", medRxiv, May 11, 2020, 41 pages.
Sharov, Konstantin S., "Creating and applying SIR modified compartmental model for calculation of COVID-19 lockdown efficiency", Elsevier, Chaos, Solitons and Fractals, Sep. 24, 2020, 14 pages.
Zugarini, Andrea et al., "An Optimal Control Approach to Learning in SIDARTHE Epidemic model", arXiv:2010.14878v1 [cs.LG], Oct. 28, 2020, 11 pages.
Cooper, Ian et al., "A SIR Model Assumption for the Spread of Covid-19 in Different Communities", Chaos Solitons Fractals, doi:10.1016/j.chaos.2020.110057, Oct. 2020, 15 pages.
Haushofer, Johannes et al., "Which Interventions Work Best in a Pandemic?", Science, vol. 368, No. 6495, 9 Pages, May 2020.
Matzinger, Polly et al., "Strong Impact of Closing Schools, Closing Bars and Wearing Masks During the Covid-19 Pandemic: Results from a Simple and Revealing Analysis", Science AAAS, 15 Pages, Sep. 2020.
Samat, Nor Azah, "Mathematical Models for Vector-Borne Infectious Disease Mapping with Application to Dengue Disease in Malaysia", PhD Thesis, University of Salford, Manchester, UK, 240 Pages, Jan. 2012.
Anonymous, "Compartmental Models in Epidemiology", Wikipedia, May 26, 2021, 25 pages.
Anonymous, "Segmented Regression", Wikipedia, May 4, 2021, 6 pages.

(56) References Cited

OTHER PUBLICATIONS

Jawa, Taghreed M., "Statistical Methods of Detecting Change Points for the Trend of Count Data", Thesis submitted to the University of Strathclyde, Glasgow, UK, for the degree of Doctor of Philosophy in the Faculty of Science, Jul. 2017, 415 pages.

\* cited by examiner

CONTROLLING COMPARTMENTAL FLOWS IN EPIDEMIOLOGICAL MODELING BASED ON MOBILITY DATA

BACKGROUND

The present application relates generally to an improved data processing apparatus and method and more specifically to mechanisms for controlling compartmental flows in epidemiological modeling.

Compartmental models are often used to represent populations with regard to infectious diseases. With such compartmental models, a population is assigned to compartments with labels corresponding to different states of the persons with regard to the disease, e.g., susceptible (S), infections (I), or recovered (R). With such modeling, people may progress between compartments with the order of the labels usually showing the flow patterns between the compartments, e.g., SEIS refers to a flow of persons from a susceptible state, exposed state, infections state, then susceptible again.

The compartmental models are used to predict how a disease spreads, the total number of infected, or the duration of an epidemic, and to estimate various epidemiological parameters, such as the reproductive number. Such models can also show how different public health interventions may affect the outcome of the epidemic, e.g., what the most efficient technique is for issuing a limited number of vaccines in a given population.

The SIR model is one example of a compartmental model, with many other models being derivatives of this SIR model. The model consists of three compartments, the number of Susceptible individuals, the number of Infectious individuals, and the number of Removed (and immune) or recovered individuals. The Susceptible compartment comprises the persons that are susceptible to the infectious disease and if brought into infections contact with an infected infections individual, will contract the disease, at which point the susceptible individual transitions to the Infectious compartment. The Infections compartment comprises the individuals who have been infected and are capable of infecting susceptible individuals. The Removed compartment comprises the individuals that have been removed either because they have become immune (recovered) or have died.

These compartments S, I, and R represent the number of people in each compartment at a particular time and thus, the number of people in each compartment may change over time even if the total population size remains constant. Each compartment may be modeled as a set of differential equations with functions being defined for the specific disease of interest. Transitions between the compartments have associated transition rates. For example, the transition rate between compartment S and compartment I is a function of the total population, the average number of contacts per person per time, multiplied by the probability of disease transmission in a contact between as susceptible and infections individual. The transmission rate between compartment I and compartment R is proportional to the number of infectious individuals such that the probability of an infectious individual recovering y in any time interval dt is simply ydt, e.g., if an individual is infectious for an average time period D, then y=1/D.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory coupled to the at least one processor and having instructions executed by the at least one processor to specifically configure the at least one processor to execute the method. The method comprises performing machine learning training of an isolation rate prediction AI computer model to generate a trained isolation rate prediction AI model that predicts an isolation rate of a biological population. The method further comprises receiving isolation data from one or more data source computing systems. The isolation data comprises mobility data providing data indicating a measure of mobility of the biological population. The method also comprises executing the trained isolation rate prediction AI model on input features extracted from the isolation data to generate a predicted isolation rate. The method further comprises executing a compartmental epidemiological computer model comprising a plurality of compartments representing states of a population with regard to an infectious disease, to simulate a progression of the infectious disease. Moreover, the method comprises controlling, during execution of the compartmental epidemiological computer model, a flow of portions of the monitored population from at least one first compartment to at least one second compartment in the compartmental epidemiological computer model based on the predicted isolation rate.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
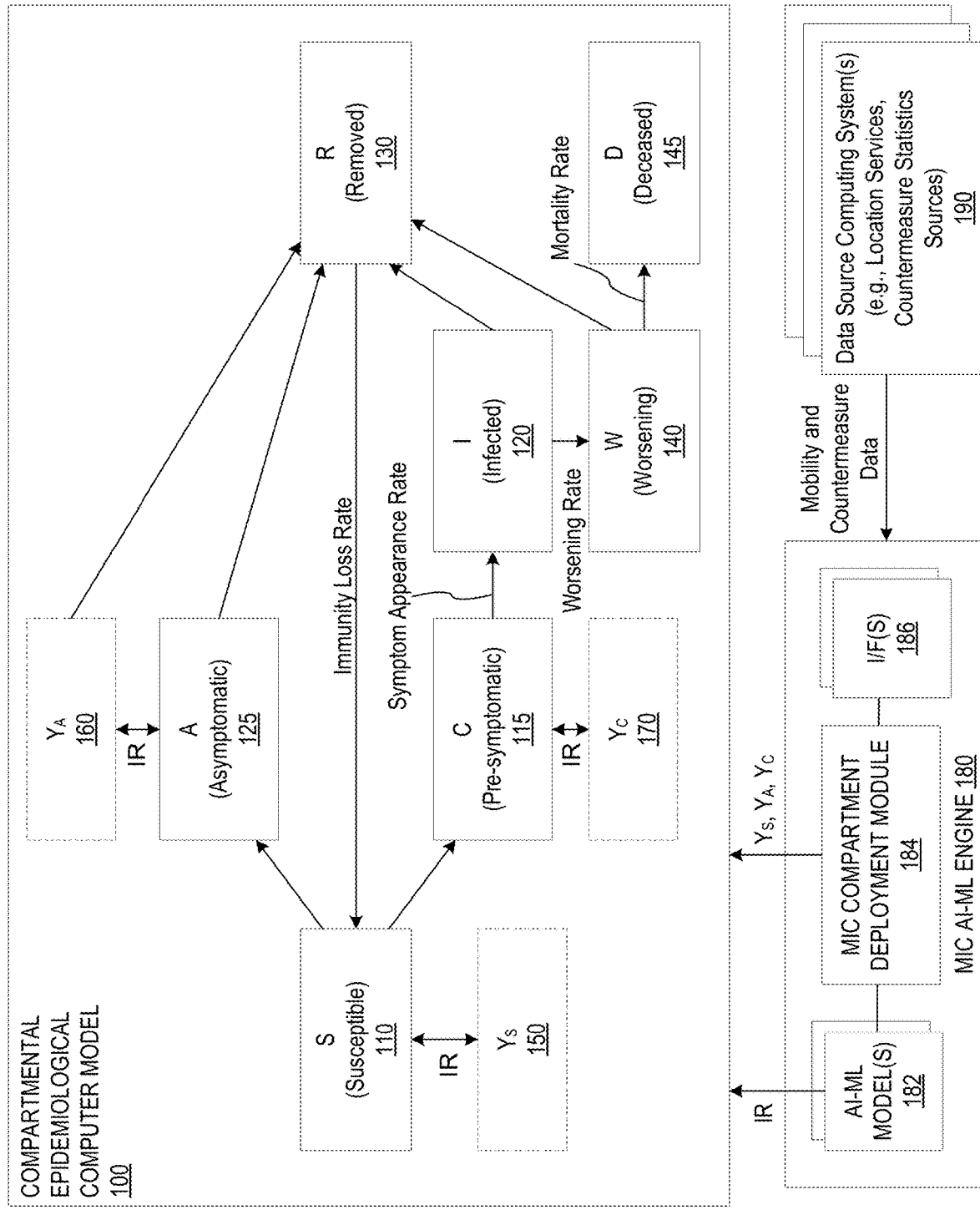
FIG. 1 is an example block diagram of a compartmental epidemiological computer model in accordance with one illustrative embodiment.

As discussed above, the compartmental models, such as SIR or SEIS models, provide insights into how infectious diseases spread in a population. One primary assumption of existing compartmental models is that the population is permitted to freely mingle, i.e., there are no restrictions on the movement of individuals in the population. This assumption affects the transition rates of individuals from one compartment to another in the compartmental model, tending to provide increased transition rates and thus, increased flow of individuals into and out of the compartments of the compartmental model. Such transition rates and flows of individuals, while providing an approximation of the actual spread of an infectious disease, do not provide an accurate depiction of the spread within a population when the individuals of the population are not free to physically interact or mingle with each other, choose not to physically interact or mingle, or have other restrictions that cause intermingling of the individuals of the population to be curtailed. This is especially true when external or self-imposed restrictions on movement are instituted, such as governmental lockdowns of the population or self-isolation for various reasons, e.g., the individuals having other comorbidities.

Thus, existing computer epidemiological models, and decision support computing systems, such as artificial intelligence based decision support computing systems, machine learning based decision support computing systems, or cognitive computing systems, implementing such existing computer epidemiological models generate incorrect results due to the inaccurate assumptions of population mobility. It would be beneficial to provide an improved computer executed epidemiological model that takes into account actual mobility data to provide an improved and more realistic representation of the physical interactions and intermingling of a population when determining transmission rates and transition rates between compartments. The illustrative embodiments provide an improved computer epidemiological model and an improved decision support computing system operating based on the improved computer epidemiological model, which provides more accurate results based on actual mobility data gathered from at least a subset of individuals in a monitored population.

The illustrative embodiments leverage additional data signals, such as aggregate mobility data and countermeasure data (e.g., data referring to governmental mandates, such as instituting of lockdowns and social distancing measures, mask mandates, and the like, which can be determined through data sources indicating the institution of such measures as well as application data, such as contract tracing applications, and the like) associated with the monitored population, e.g., the mandates applicable to the geographical region of the monitored population, to tune the flow (transition) of individuals in and out of compartments in a computer executed compartmental model of an infectious disease, such as from a compartment corresponding to susceptible segment of a population, to an asymptomatic compartment or a pre-symptomatic compartment, etc. The illustrative embodiments incorporate additional signals within computer executed epidemiological modeling to control the flow between various compartments using an artificial intelligence (AI) and machine learning (ML) based computer framework and data-driven approach. AI and ML based frameworks allow the illustrative embodiments to fine tune parameters of the epidemiological model automatically based on gathered data, such as mobility data gathered from mobile computing devices, e.g., mobile smartphone devices, vehicle mounted computing systems, portable computing devices, health tracker computing devices, and the like, associated with at least a subset of a monitored population. For example, the mobility data gathered from the mobile computing devices is used, potentially along with other data, such as countermeasure data, to adjust the population pools of various compartments in the compartmental epidemiological computer model based on modeled transmission rates of the disease within a population.

The illustrative embodiments use the AI-ML based computer framework to create implicit and explicit mapping from these additional signals (e.g., mobility and countermeasure signals) into a function that controls flows into various compartments with the overall AI-ML based computer framework providing computer logic for auto-tuning various parameters of the AI-ML based computer framework and/or epidemiological computer model(s) that operate as part of the AI-ML based computer framework. For example, flow parameters which change over time may be estimated and predicted using the AI-ML based computer framework and applied to the transitions between compartments in a compartmental epidemiological computer model. In so doing, the mechanisms of the illustrative embodiments allow for granular epidemiological modeling with adjustments of flow (transition) parameters based on temporal and geographical region (e.g., particular populations) factors, allows for automatic fine tuning of flow (transition) parameters affecting the populations of each compartment in the epidemiological computer model over time, and improves the accuracy of the epidemiological computer model projections by basing such projections on actual mobility and countermeasure data of actual populations, or at least a subset of the actual populations.

In one illustrative embodiment, a set of differential equations may be provided for each compartment in the compartmental model where these differential equations, for a compartment, model the flow of people into/out of the corresponding compartment, i.e. the changes in state of the population for each compartment at any time instance. As will be described herein, mobility information may be directly integrated into the modeling by providing logic for (a) smoothening changes in mobility data over a predetermined period of time, e.g., the daily change in mobility, (b) interpolating the data so that it is has a continuous value (e.g., the mobility at time 122.3 can be determined, which is needed by the differential equation), and (c) logic is provided for determining the interpolated isolation rates for the compartments. This isolation rate equation may be passed as external parameter such that it is not tuned by the differential equations. In other words, the illustrative embodiments incorporate the mobility information without requiring an additional learnable parameter, which would increase the model complexity and result in overfitting.

In accordance with one illustrative embodiment, a compartmental model augmented to include considerations of mobility data for a population may include compartments for susceptible (S) portions of the population, infected (I) portions, asymptomatic (A) portions, pre-symptomatic (C), removed/recovered (R) portions, worsening (W) portions, deceased (D) portions, and the like, as well as corresponding isolation compartments (Y), modeling interventions causing isolation of portions of the population. As the time scale is continuous, interpolation functions are added on any of the tertiary sources that directly control the flow, e.g., changes in mobility that controls population movement or transitions T from a first compartment, for example compartment S, to a second compartment, for example compartment Y. An example of these equations, in accordance with one illustrative embodiment, may be the following set:

$$T_{Y \to S} = \max(0, f_{mob}(t)) \quad (1)$$

$$T_{S \to Y} = \max(0, -1 * f_{mob}(t)) \quad (2)$$

where $f_{mob}$ is the fitted function used to extrapolate mobility data to get likely mobility values in the future. The compartment flow rates may be defined, in one illustrative embodiment, for the S and Y compartments, as the following:

$$\frac{dS}{dt} = -\beta * \frac{S*(I+A+C)}{N} + \rho * R +$$
$$\min(Y, T_{Y \to S} * (S+Y)) - \min(S, T_{S \to Y} * (S+Y))$$

$$\frac{dY}{dt} = \min(S, T_{S \to Y} * (S+Y)) - \min(Y, T_{Y \to S} * (S+Y))$$

$$\frac{dA}{dt} = (1-\xi) * \left(\beta * S * \frac{I+A+C}{N}\right) - \gamma_A * A$$

$$\frac{dC}{dt} = (\xi) * \left(\beta * S * \frac{I+A+C}{N}\right) - \alpha * C$$

$$\frac{dI}{dt} = \alpha * C - (\gamma_I + \omega) * I$$

$$\frac{dW}{dt} = \omega * I - (\mu_d + \gamma_W) * W$$

$$\frac{dR}{dt} = \gamma_I * I + \gamma_A * A + \gamma_W * W - \rho * R$$

$$\frac{dD}{dt} = \mu_d * W$$

where $\beta$ is a time varying transmission rate parameter, $\rho$ is an immunity loss rate, $\xi$ is a case reporting rate, $\omega$ is a time delay, $\gamma$ is a recovery rate from the respective compartment state, $\mu_d$ is a death rate, and the values S, I, A, C, W and Y are the populations of the corresponding compartments, and N is a total population. The transmission rate represents the likelihood that a person will be infected and the case reporting rate represents the likelihood that a person will be tested for the infectious disease if not showing symptoms. This is just an example of one set of differential equations that may be used to model aspects of an infectious disease using a compartmental model, and are not intended to be limiting on the illustrative embodiments. Many modifications may be made to these examples without departing from the spirit and scope of the present invention.

Before discussing the various aspects of the illustrative embodiments and the improved computer operations performed by the illustrative embodiments further, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on hardware to thereby configure the hardware to implement the specialized functionality of the present invention which the hardware would not otherwise be able to perform, software instructions stored on a medium such that the instructions are readily executable by hardware to thereby specifically configure the hardware to perform the recited functionality and specific computer operations described herein, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the illustrative embodiments are specifically directed to an improved computing tool and improved computing tool operation that improves the way in which compartmental epidemiological computer models model the progression of an infectious disease with regard to a given population and provides a more accurate representation given various measures for isolating individuals within the population. The illustrative embodiments are specifically concerned with the computer modeling of such infectious diseases and solving the deficiencies of existing computer models in this regard which assume a freely interacting population. By improving the computer modeling of infectious diseases in this manner, improved predictions are provided which improves the accuracy of the decision support computing systems that rely on these epidemiological computer models.

FIG. 1 is an example block diagram of a compartmental epidemiological computer model in accordance with one illustrative embodiment. The epidemiological computer model is shown as a set of connected boxes representing different compartments, where each compartment has a population of individuals whose state, with regard to the progression of the infectious disease being modeled, corresponds to a pre-defined state of progression of the disease, e.g., susceptible, asymptomatic, pre-symptomatic, infected, recovered/removed, worsening, deceased, etc. Connections between the boxes represent the flow, or transitions, from one state to another, with each connection having a transition rate indicating the amount of flow over time of individuals in a first connected compartment into a second connected compartment. Each of the connected boxes have corresponding computing logic associated with them for modeling the population of the compartment and the transitions to/from the compartment.

The particular compartmental epidemiological computer model shown in FIG. 1 represents a computer model representation of Corona Virus Disease 2019 (COVID-19). However, it should be appreciated that this is only an example and the mechanisms of the illustrative embodiments may be implemented with an epidemiological computer model for any infectious disease that is the subject of computer modeling, such as influenza, west Nile virus, the common cold, severe acute respiratory syndrome (SARS), or any of a plethora of other infectious diseases. Moreover, the depicted computer model has specific compartments and transitions between compartments that are for an example implementation of the COVID-19 epidemiological computer model and other epidemiological computer models may have different compartments from those shown in FIG. 1, yet are intended to be within the spirit and scope of the present invention.

As shown in FIG. 1, similar to the SIR model discussed previously above, the example illustrative embodiment in FIG. 1 has compartments 110, 120, and 130 for susceptible individuals (S), infected individuals (I), and recovered/removed individuals (R), respectively. In addition, compartments 115 and 125 are provided to represent the pre-symptomatic individuals (C) and the asymptomatic individuals (A). The susceptible individuals (S) 110 represent the portion of the population P that have not been determined to be infected and thus, are not asymptomatic (yet infected), pre-symptomatic (yet infected), infected, or have been removed/recovered, i.e., are immune to the infectious disease. The asymptomatic individuals (A) 125 represent the portion of the population P that have been infected but are not showing any symptoms of the disease, i.e. they are asymptomatic, or are individuals that are unreported. The individuals in compartment A 125 represent potential spreaders of the infectious disease due to these individuals being infected but not knowing of the infection since they do not show symptoms.

The pre-symptomatic individuals (C) 115 represent the portion of the population P that have been infected but are not showing symptoms of the disease yet because the disease is in an incubation time frame of the disease within the individuals, e.g., some individuals may be infected, yet not show symptoms for a few days after being infected. Again, these individuals in compartment C 115 represent potential spreaders of the infectious disease due to these individuals being infected but not knowing of the infection since they are not exhibit symptoms yet.

The infected individuals (I) 120 represents the portion of the population P that have been infected and are showing symptoms of the disease. The removed/recovered individuals (R) 130 represents the portion of the population P that were infected (e.g., asymptomatic or infected) but have recovered and thus, are immune. It should be appreciated that for some diseases, such as COVID-19, there is a possibility of a loss of immunity, such as due to variants of the disease or the like, and this is represented by a transition from the removed/recovered compartment 130 back to the susceptible compartment 110.

In addition to these compartments 110-130, compartment W 140 represents a portion of the population P that is infected and whose condition is worsening. This worsening compartment W 140 represents the time delay between when an individual is infected and shows symptoms of the infection, and when the individual dies from the infectious disease, represented by the deceased (D) compartment 145. That is, there is a time period where the health of the individual worsens over time before the individual dies of the disease and this is represented by compartment W 140.

Transitions or connections between compartments 110-145 represent a flow of portions of population from one state of the disease to another. Each of these transitions have transition rates associated with them that represent the number of individuals per time unit whose state of the disease changes from an initial state (tail of the arrow) to a changed state (head of the arrow). For example, the transition from the susceptible compartment S 110 to the asymptomatic compartment A 125 represents the number of individuals per time unit that are infected by do not show any symptoms.

The data needed to determine the transition rate from S 110 to A 125 may be obtained, for example, from case reporting performed by health and/or governmental organizations which collect such data, such as the Centers for Disease Control (CDC), World Health Organization (WHO), hospital networks, state and local government organizations, or the like. For example, the transition rate from compartment S 110 to compartment A 125 for COVID-19 may be determined from historical statistical data gathered by one or more data collection source computing systems, such as data gathered and reported by the CDC and/or WHO, which specifies case reports where the individual reported no symptoms but tested positive for the virus.

Similarly, such statistical data from case reporting data gathering and reporting computing systems, such as the CDC and/or WHO computing systems, may also specify individuals that tested positive and then showed symptoms as well as the time delay between testing positive and showing symptoms, which indicates the incubation time of the disease and can be used to determine the transition rate from compartment S 110 to compartment C 115, and then from compartment C 115 to compartment I 120. The transition from compartment C 115 to compartment I 120 represents the symptom appearance rate. Moreover, such statistical data from case report gathering and reporting computing systems may include other data specifying statistics as to immunity loss of recovered/removed individuals, numbers of infected individuals that die from the disease, and timing, such as numbers of days between infection and death/recovery. The various rates associated with the transitions may be determined from these statistics and gathered case report data in a manner readily apparent to those of ordinary skill in the art.

It can be appreciated from the above description that the portions of the population P that are present in the various compartments 110-145 at any one time is dependent upon the modeling of the spread of the disease based on the transitions between compartments 110-145, which in turn is based on the time dependent case reporting and time dependent determined transmission rate of the disease, i.e., how much an infected person will infect the population P over a given period of time. The transmission rate of the disease is determined based on an assumption that the population is not restricted in its mobility and thus, each individual has the same amount of opportunity to infect the same amount of the population P over a given period of time. However, when compared to the reality of mobility restrictions, such as lockdowns, self-isolation, and the like, such assumptions render the modeling of the disease inaccurate. Moreover, various countermeasures that may be employed by individuals within the population P may lessen the ability of the infectious disease to spread throughout the population P, e.g., reduction in public transport, reduced store hours, wearing masks, social distancing, etc.

In accordance with the illustrative embodiments, additional mobility isolation and countermeasure (MIC) compartments 150-170 are provided to model a realistic adjustment to the portions of the population P that are present in selected compartments 110-145 of the compartmental epidemiological computer model 100. For example, in the depicted compartmental epidemiological computer model 100, MIC compartment $Y_S$ 150 is connected with compartment S 110, MIC compartment $Y_A$ 160 is connected with compartment A 125, and MIC compartment $Y_C$ 170 is connected with compartment C 115. Thus, MIC compartment 150 represents the portion of the population of S that is not mobile (e.g., currently under a lockdown order from the government, perform self-isolation due to co-morbidities, or the like) and/or is implementing countermeasures to the disease (e.g., washing hands, wearing masks, social distancing, etc.) as determined from real-world data, as discussed hereafter. Transitioning a portion of the population of compartment S 110 to MIC compartment 150 takes that portion of the population out of the flow from compartment S to compartment A or compartment C as those individuals are not susceptible to infection by the disease due to them not being exposed to the infectious disease through assumed free mingling with other individuals in the population. It should be appreciated that the connection between compartment S 110 and MIC compartment 150 is a two-way connection since the transition is time dependent, e.g., lockdown orders are imposed/lifted, intensified, etc., and individuals in greater/lesser numbers engage in self-isolation and countermeasures, e.g., mask mandates may be lifted and thus, individuals may stop wearing masks making them more susceptible.

Similar considerations apply to the other MIC compartments 160 and 170. MIC compartment 160 represents the portion of the population of asymptomatic individuals in compartment 125 that are not mobile or are engaged in countermeasures to help lessen the spread of the infectious disease. By transitioning a portion of the population of compartment A to MIC compartment 160, the transitioned portion represents the portion that is not spreading the disease to others. Similarly, by transitioning a portion of the population of compartment C 115 to MIC compartment 170, the transitioned portion represents the portion of pre-symptomatic individuals that are not spreading the disease to others. Thus, by moving population from compartments 115 and 125, the population transitioned does not contribute to the force of infection.

The MIC compartments 150-170 are pluggable into an existing compartmental epidemiological computer model 100 and do not require additional parameters for the compartmental epidemiological computer model 100. To the contrary, the MIC compartments 150-170 represent compartments in which a sub-portion of the populations in each of the attached compartments of the epidemiological computer model 100 are placed due to restrictions in mobility and/or countermeasures employed by the corresponding portions of the population of those epidemiological computer model compartments. Thus, in order to integrate the MIC compartments 150-170 into a compartmental epidemiological computer model 100, all that is needed is to know which compartments of the epidemiological computer model 100 are to have associated MIC compartments, e.g., compartments 110, 115, and 125 and corresponding MIC compartments, e.g., MIC compartments 150-170, may be automatically generated for these designated compartments in the compartmental epidemiological computer model.

The characteristics, e.g., transitions rates, of the transitions from and to these epidemiological computer model compartments to and from the MIC compartments 150-170 are learned through the application of trained AI-ML based computer models 182 of a MIC AI-ML engine 180 that take gathered mobility and countermeasure data from data source computing systems 190 and predict the mobility and countermeasure use of the population over time. The MIC AI-ML engine 180 comprises a MIC compartment deployment module 184 that deploys the MIC compartments, such as MIC compartments 150-170, into the compartmental epidemiological computer model 100 based on configuration information specifying which compartments of the compartmental epidemiological computer model are to have their flows modified by isolation rates determined by the trained AI-ML based computer models 182 of the MIC AI-ML engine 180, such as compartments 110, 115, and 125 of the depicted example epidemiological computer model 100. In this way, the MIC compartments 150-170 are deployed into an epidemiological computer model in a plug-in manner and do not require modification of the existing epidemiological computer model. The MIC AI-ML engine 180 further includes interfaces 186 for obtaining mobility and countermeasure data from data source computing systems 190.

The AI-ML based computer model(s) 182 may be trained, through a machine learning based process, such as supervised machine learning, based on historical mobility data and countermeasures use statistics data, to predict the transition rate to/from MIC compartments 150-170. These transition rates represent the rate at which individuals are isolated, due to externally imposed or self-imposed isolation measures, and/or the rate at which individuals isolate themselves from becoming infected or spreading the infectious disease by use of countermeasures. These transition rates are time dependent and patterns of these transition rates may be learned over time such that timing factors may also be included in the AI-ML based computer model(s) 182, e.g., the infectious disease may not be spread as easily in warmer months of the year than in colder months of the year, the infectious disease may be spread at a higher rate over holiday weekends, etc.

The mobility data gathered from the data source computing systems 190 may be mobility data that is collected through known mobility and/or location detection and monitoring systems based on tracking of mobile computing devices associated with individuals of a monitored population, which may be an entire population or a subset of a population of a given geographical region, for example. It should be appreciated that the mobility data does not need to be tied to the spread of diseases, let alone the spread of the particular infectious disease being modeled by the compartmental epidemiological computer model. To the contrary, the mobility data may be general mobility data that is concerned with representing how mobile a given population is. For example, the mobility data may simply represent locations of mobile devices over a predetermined period of time. An individual within the mobility data may be considered "mobile" if their location changes by a predetermined amount, and the number of times that the location changes by the predetermined amount over the predetermined period of time meets or exceeds a predetermined threshold amount, e.g., the individual travels equal to or more than 5 miles at least 5 times within a week time period.

Numbers or percentages of individuals classified as mobile within the population may be tracked over time to determine how these numbers or percentages change over time such that learned associations between mobility and other time based factors may be determined and thus, predictions of mobility based on time based factors may be made by the trained AI-ML based computer model. Moreover, mobility may be mapped, through the AI-ML based computer model, to a transition rate for the transitions to/from the MIC compartments from/to the compartments of the epidemiological computer model. For example, it may be determined that mobility of individuals falls from one time period to another time period by 3%. Thus, a greater number of individuals, e.g., 3% more, should transition from compartment S 110 to MIC compartment 150, however in another time period the mobility may increase by 2% such that the transition from compartment S 110 to MIC compartment 150 should be reduced, e.g., reduced by 2% which, given the example 3% increase mentioned above gives a net transition from compartment S 110 to MIC compartment 150 of 1% increase over a baseline. The change in the mobility, although observed at discrete time periods (e.g., daily), is transformed into a continuous function for the AI-ML based computer model such that the mobility may be queried to get the change in the mobility at any time instance (e.g., any fraction of the day).

Thus, the AI-ML based computer model(s) 182 are trained through machine learning to identify patterns in input features indicative of different levels of isolation. These features may be extracted from data gathered from various data source computing systems 190 and may include features such as levels of mobility of individuals specified in one or more types of mobility data from data source computing systems 190 and/or countermeasure data specifying statistical measures of the population with regard to implementing one or more countermeasures for isolating individuals from being infected or infecting others, e.g., wearing masks, using hand sanitizer, washing hands, social distancing, and the like, of the population. The AI-ML based computer model(s) 182 determine or predicts an isolation rate based on the identified patterns, which is then applied to the connections between the selected compartments of the epidemiological computer model 100, e.g., compartments 110, 115, and 125 in FIG. 1, to thereby modify the populations of these compartments by transitioning individuals from the compartments 110, 115, and 125 to corresponding MIC compartments 150-170 according to the isolation rate. It should be appreciated that as individuals in the population take more measures to isolate themselves from each other and take countermeasures to reduce the spread of the infectious disease, the isolation rate increases and thus, more of the population of the compartments in the epidemiological computer model 100 transition to the MIC compartments 150-170. As individuals in the population reduce measures to isolate themselves from each other and/or relax countermeasures, the isolation rate decreases and thus, less of the population of the compartments in the epidemiological computer model 100 transition to the MIC compartments 150-170 and/or more of the population of the MIC compartments 150-170 transitions based to the corresponding compartments 110, 115, and 125 of the epidemiological computer model 100.

In some illustrative embodiments, the data source computing systems 190 comprise computing systems that gather and report mobility data of mobile devices associated with individuals of a monitored population. For example, location services, such as provided by Google™ or Apple™ in association with their mobile phone devices may be used to track movements of individuals in a population, given authorization of these individuals to such tracking of movements. Such mobility data may be used to determine statistical representations of the amount and degree of mobility of the monitored population which may then be used with the AI-ML based computer model 180 to predict isolation rates for transitioning populations in compartments of an epidemiological computer model into and out of MIC compartments 150-170 which model the isolation of the population.

It should be appreciated that the mobility data is not limited to mobility data gathered from the tracking of movement of mobile computing devices by mobility and/or location tracking services. Other mobility data that may be used includes vehicular traffic information that may be gathered and reported by highway management organizations, toll road management organizations, airline reservation systems, or any other source of data indicative of the general mobility of a population. Various different types of mobility data may be used together to obtain a representation of the mobility of a given population or at least a subset of the population. For example, features extracted from each type of mobility data may be provided as inputs to the AI-ML computer model(s) 182 as input features in which the AI-ML computer model(s) 182 identify patterns for correlating with different levels of isolation and predicted isolation rates.

The same is true of countermeasures data which may comprise various types of countermeasure data such as statistics on mask wearing, statistics on hand washing, statistics on hand sanitizer usage, statistics on social distancing, etc. Features extracted from each of these different types of countermeasure data may be input to the AI-ML computer model(s) 182 as separate countermeasure features in which the AI-ML computer model(s) 182 identifies patterns and for correlating with different levels of isolation and predicted isolation rates.

Moreover, in some illustrative embodiments, the AI-ML computer model(s) 182 may comprise a plurality of differently trained AI-ML computer models 182 for separately processing mobility data and countermeasure data. In other illustrative embodiments, the AI-ML computer model(s) 182 may comprise a single AI-ML computer model 182 that receives a combination of feature inputs of both mobility and countermeasure data as input upon which the single AI-ML computer model 182 operates to predict an isolation rate. In the case of an illustrative embodiment in which a plurality of differently trained AI-ML computer models 182 are utilized, the AI-ML computer models 182 may further include aggregation logic that aggregates the isolation rate predictions generated by the other AI-ML computer models 182 in the plurality. The particular function for aggregating the predictions may be implementation dependent and may also be trained using a machine learning of empirical methodology. For example, the function may be a weighted aggregation function that applies different learned weight values, learned through machine learning or empirical evaluation, to different ones of the isolation rate predictions generated by the other AI-ML computer models 182.

Thus, the illustrative embodiments provide an additional AI-ML computer model mechanism that augment and improve compartmental epidemiological computer models. The mechanisms of the illustrative embodiments provide for granular modeling of adjustments to flow parameters according to temporal changes in isolation features of a population, e.g., features indicating the mobility of the population and countermeasures instituted by individuals of the population. It should be appreciated that this granular and temporal modeling of isolation features may be performed for various levels of geographic regions. For example, different AI-ML computer models 180 may be provided for different populations for different geographical regions, such as cities, counties, states, countries, territories, continents, etc., i.e., any desired population.

The mechanism of the illustrative embodiments provide additional AI-ML computer model logic that provides for automatic tuning of flow parameters governing flows of portions of a population between compartments of a compartmental epidemiological computer model. In some illustrative embodiments, the automatic tuning is implemented by providing MIC compartments which model the relative isolation of individuals of the population due to restrictions on mobility and/or countermeasures instituted. As new data is gathered and reported by data source computing systems 190, the flow parameters are automatically updated by the AI-ML computer model logic which predicts isolation rates based on identified patterns in features extracted from the gathered and reported data. Such modeling may also predict for a future time what the likely isolation rate will be based on expected input features at that time, as determined from historical data. For example, temporal features may be input to the AI-ML computer model 180 which, having learned from historical data patterns of isolation rates increase/decrease during different times, may use these temporal features to determine a timing for the prediction and, along with other input features, such as those extracted from current mobility data and countermeasure data, predict an isolation rate for a future time.

By incorporating realistic mobility and countermeasures data into the modeling of infectious diseases via compartmental epidemiological computer models through the implementation of the isolation rate prediction mechanisms and MIC compartment mechanisms of the illustrative embodiments, improved accuracy in the epidemiological projections are made possible. That is, the inaccuracies in epidemiological computer models due to the unrealistic assumptions of a freely interacting population when isolation measures and countermeasures are implemented by individuals of the population. Thus, for example, for any given time point, the portions of a population that are present in each compartment of the epidemiological computer model may be determined, e.g., indicating how much of the population is susceptible, infected, asymptomatic, pre-symptomatic, recovered, worsening, deceased, etc., and these values will be more accurate than existing epidemiological computer models since the improved computer modeling of the illustrative embodiments takes into consideration the actual mobility of the population and actual implementation of countermeasures by the population, factors which both affect the flow of portions of the population into and out of compartments of the epidemiological computer model.

Figure 2:
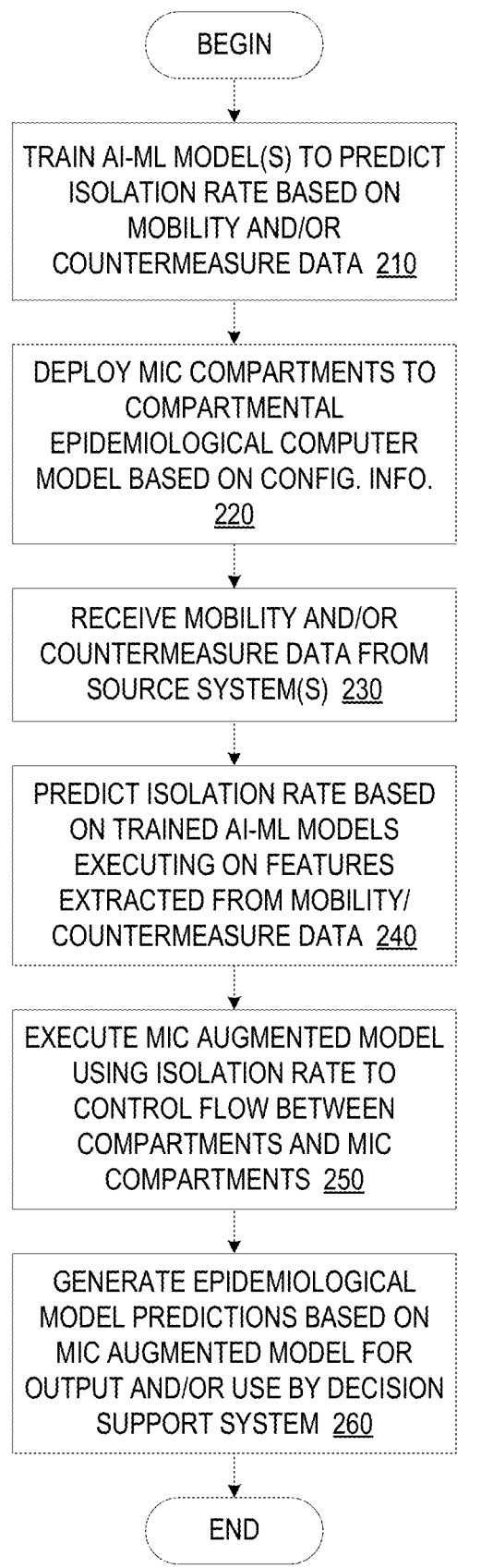
FIG. 2 is a flowchart outlining an example operation of a mobility isolation and countermeasures augmented epidemiological computer model in accordance with one illustrative embodiment.

FIG. 2 is a flowchart outlining an example operation of a mobility isolation and countermeasures augmented epidemiological computer model in accordance with one illustrative embodiment. The operation outlined in FIG. 2 may be implemented by a mobility isolation and countermeasures (MIC) artificial intelligence-machine learning (AI-ML) based engine in accordance with one illustrative embodiment, such as MIC AI-ML engine 180 in FIG. 1, for example. It should be appreciated that the operations outlined in FIG. 2 are specifically performed automatically by an improved computer tool of the illustrative embodiments and are not intended to be, and cannot practically be, performed by human beings either as mental processes or by organizing human activity. To the contrary, while human beings may initiate the performance of the operation set forth in FIG. 2 and may make use of the results generated as a consequence of the operations set forth in FIG. 2, the operations in FIG. 2 themselves are specifically performed by the improved computing tool in an automated manner.

As shown in FIG. 2, the operation starts by training, through a machine learning process, AI-ML computer model(s) to predict isolation rates based on mobility and/or countermeasure data (step 210). The machine learning operation may include the use of training data and known, i.e., ground truth, data indicating correct results to be generated by a fully trained AI-ML computer model. The training data is input to the AI-ML computer model, processed to generate a prediction of isolation rates, and the prediction is compared to the ground truth to determine an error or loss between the prediction generated and the correct prediction. The operational parameters of the AI-ML computer model that contributed to the prediction are then adjusted to attempt to reduce this error to or below an acceptable level as defined by a threshold error value. This process is repeated through multiple epochs until the AI-ML computer model converges, i.e., error is equal to or below the threshold, or a predetermined number of epochs are performed. At this point, the AI-ML computer model is determined to be trained. The AI-ML computer model may then be tested or verified using a testing/verification data set, and if the performance of the AI-ML computer model is satisfactory, the AI-ML computer model is deployed for runtime use.

Step 210 in FIG. 2 is intended to cover this process, the result of which is a set of one or more trained AI-ML computer model(s) that are able to generate predictions of isolation rates based on a set of features input to the model, where these features may include features extracted from mobility and/or countermeasure data, such as previously described above. In some illustrative embodiments, the one or more trained AI-ML computer model(s) may be a single trained AI-ML computer model that operates on both features extracted from mobility and countermeasure data, while in other illustrative embodiments separate AI-ML computer models are used for mobility and countermeasure data features. In some illustrative embodiments, only one or the other of mobility and/or countermeasure data may be utilized to predict isolation rates.

It should also be appreciated that other input features may be utilized as well, such as temporal input features, that provide additional basis for pattern recognition in the input features and corresponding prediction of isolation rates.

During runtime processing, such additional features may be obtained from parameters of the compartmental epidemiological computer model that is being executed. For example, the compartmental epidemiological computer model may be executed for a future time in order to predict the state of an infectious disease with regard to a given population at this future time. The future time, as well as other parameters, may be provided as additional input features to the trained AI-ML computer model(s) which may use the training of the AI-ML computer model(s) based on historical patterns of progression of an infectious disease and patterns of mobility and/or countermeasure use over time as an additional factor in predicting isolation rates.

Based on configuration information for the deployment of mobility isolation and countermeasure (MIC) compartments into a given compartmental epidemiological computer model, MIC compartments are deployed into the compartmental epidemiological computer model to simulate portions of populations that are isolated due to lack of mobility and/or implementation of countermeasures (step 220). That is, portions of the population are not freely intermingling with other portions of the population, or are taking precautions that effectively isolate them from the other individuals of the population with regard to spreading of an infectious disease. Thus, these individuals are simulated by the MIC compartments and the isolation rates. The deployment of MIC compartments may comprise generating the MIC compartments and providing an interface between the computer logic of the MIC compartments and the computer logic of the compartments to which the MIC compartments are connected in the compartmental epidemiological computer model. The particular compartments in the compartmental epidemiological computer model to which the MIC compartments are connected may be specified in the configuration information for the deployment.

Having deployed the MIC compartments, mobility and/or countermeasure data is obtained from data source computing systems, such as location services computing systems, government reporting computing systems, and the like, and features are extracted from the received data for use by the trained AI-ML computer model(s) (step 230). The extracted features are input to the trained AI-ML computer model(s) which generate isolation rate predictions based on the features (step 240). The generated isolation rates are then used in the execution of the MIC compartment augmented epidemiological computer model to control the flow of portions of population into/out of the MIC compartments (step 250). The compartmental epidemiological computer model augmented with the MIC compartments executes to generate predictions of infectious disease and population state which may then be output for use by a human user, e.g., a display of the results may be generated, or output to a decision support computing system (AI computing system) which may perform additional operations based on the predictions (step 260). For example, in illustrative embodiments where the output is provided to a decision support computing system, the decision support computing system may automatically generate recommendations for curtailing the predicted spread of the infectious disease. The operation then terminates.

It should be appreciated that the illustrative embodiments specifically utilize AI-ML computer models that are trained through machine learning processes to predict an isolation rate based on features from mobility and/or countermeasure data. The specific AI-ML computer models utilized will depend on the desired implementation and may be of various types. For example, the AI-ML computer models may be convolutional neural networks (CNNs), deep neural networks (DNNs), Support Vector Machines (SVMs), random forest computer models, rules based engines with machine learning used to learn parameters of the rules, or any other currently known or later developed machine learning based computer model used to implement artificial intelligence operations.

It should as be appreciated that while the primary illustrative embodiments are directed to modeling infectious diseases with regard to human populations, the illustrative embodiments are not limited to such. To the contrary, the epidemiological computer models with which the mechanisms of the illustrative embodiments may be implemented may be used to model infectious diseases for any biological organism, such as the spread of viruses within animal populations or the like.

As noted above, the illustrative embodiments are specifically directed to an improved computing tool and improved computing tool operation that improves the way in which compartmental epidemiological computer models model the progression of an infectious disease with regard to a given population and provides a more accurate representation given various measures for isolating individuals within the population. The illustrative embodiments specifically provide an artificial intelligence computer tool that is trained through machine learning training to recognize patterns in mobility and countermeasures data of various types to predict an isolation rate of a given population. The isolation rate is then applied to each of one or more mobility isolation and countermeasure (MIC) compartments that are added to a compartmental epidemiological computer model so as to adjust the flows of portions of the population between compartments of the epidemiological computer model. The isolation rate and MIC compartments model the individuals of the population that are isolated or less likely to contract or spread the infectious disease due to their isolation and/or use of countermeasures. By integrating isolation and countermeasure factors into the control of the flow of portions of the population between compartments of a compartmental epidemiological computer model, the deficiencies of existing epidemiological computer models which assume a freely interacting population are minimized. By improving the computer modeling of infectious diseases in this manner, improved predictions are provided which improves the accuracy of the decision support computing systems that rely on these epidemiological computer models.

Figure 3:
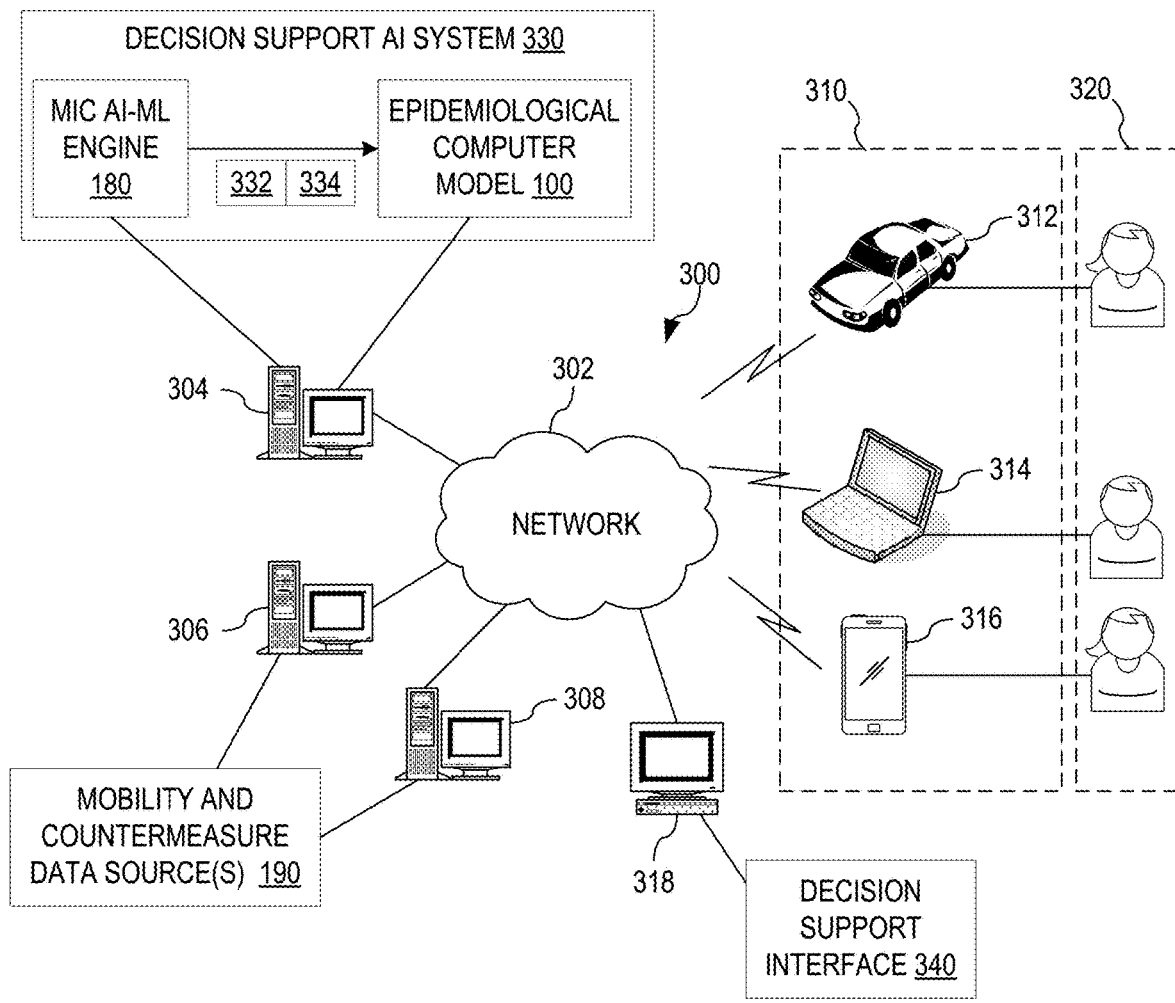
FIG. 3 is an example diagram of a distributed data processing system in which aspects of the illustrative embodiments may be implemented.
Figure 4:
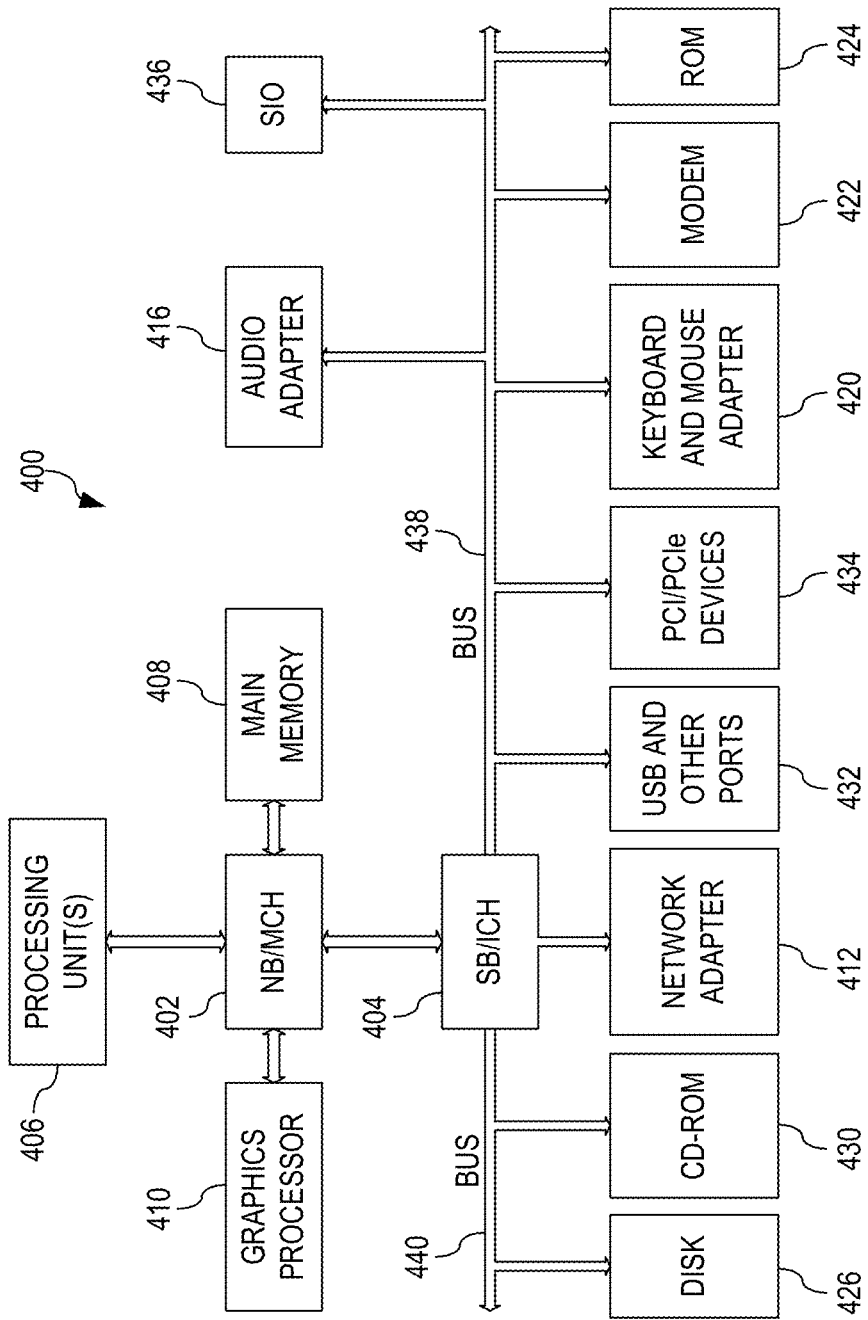
FIG. 4 is an example block diagram of a computing device in which aspects of the illustrative embodiments may be implemented.

Thus, the illustrative embodiments may be utilized in many different types of data processing environments. In order to provide a context for the description of the specific elements and functionality of the illustrative embodiments, FIGS. 3 and 4 are provided hereafter as example environments in which aspects of the illustrative embodiments may be implemented. It should be appreciated that FIGS. 3 and 4 are only examples and are not intended to assert or imply any limitation with regard to the environments in which aspects or embodiments of the present invention may be implemented. Many modifications to the depicted environments may be made without departing from the spirit and scope of the present invention.

FIG. 3 depicts a pictorial representation of an example distributed data processing system in which aspects of the illustrative embodiments may be implemented. Distributed data processing system 300 may include a network of computers in which aspects of the illustrative embodiments may be implemented. The distributed data processing system 300 contains at least one network 302, which is the medium used to provide communication links between various devices and computers connected together within distributed data processing system 300. The network 302 may include connections, such as wire, wireless communication links, or fiber optic cables. The at least one network 302, and the computing devices that make up the network, may constitute a cloud computing system in which aspects of the illustrative embodiments may be implemented. For example, the various computing devices, servers, switches, routers, client computing devices, etc., may operate together such that the servers provide cloud services to the client computing devices via the other computing devices, switches, routers, and the like, of the at least one network 302.

In the depicted example, servers 304-308 are connected to network 302, which may have a plethora of other computing devices, and infrastructure devices, such as storage systems, routing devices, and the like (not shown). In addition, client devices 310 are also connected to network 302. These client devices 310 may be, for example, personal computers, network computers, or any other currently known or later developed data processing device or system that is capable of communicating data to and/or receiving data from the wired or wireless data connections of the at least one network 302. In accordance with the illustrative embodiments, the client computing devices 310 are wireless mobile computing devices associated with users of a population 320. For example, as shown in FIG. 3, one client computing device 312 may be a computing system installed in a vehicle, such as an automobile or the like. Another client computing device 314 may be a mobile computing device, such as a laptop, personal digital assistant (PDA), health tracker computing device (such as a FitBit™, iWatch™, or the like), or other mobile computer. Still another client computing device 316 may be a mobile communication device, such as a smart phone, for example, that has a computing and wireless data communication capability. In accordance with the illustrative embodiments, the client computing devices communicate with the network 302 via wireless communication connections due to their being mobile devices with the intent that the mobility of these devices is indicative of the mobility of the corresponding users in the population 320.

In some illustrative embodiments, one or more of the servers 304-308 may provide data, such as boot files, operating system images, and applications to the client computing devices 310, with the client computing devices 310 being clients to the servers 304-308 in the depicted example. Distributed data processing system 300 may include additional servers, clients, and other devices not shown.

In the depicted example, distributed data processing system 300 is the Internet with network 302 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 300 may also be implemented to include a number of different types of networks, such as for example, an intranet, a local area network (LAN), a wide area network (WAN), or the like. As stated above, FIG. 3 is intended as an example, not as an architectural limitation for different embodiments of the present invention, and therefore, the particular elements shown in FIG. 3 should not be considered limiting with regard to the environments in which the illustrative embodiments of the present invention may be implemented.

As shown in FIG. 3, one or more of the computing devices, e.g., server 304, may be specifically configured to implement a decision support artificial intelligence (AI) computing system 330 which includes a mobility isolation and countermeasures (MIC) AI-ML engine 180 and compartmental epidemiological computer model 100. In addition, one or more of the servers 306-308 are configured to operate a mobility and/or countermeasure data source(s) 190. The configuring of the computing devices may comprise the providing of application specific hardware, firmware, or the like to facilitate the performance of the operations and generation of the outputs described herein with regard to the illustrative embodiments. The configuring of the computing devices may also, or alternatively, comprise the providing of software applications stored in one or more storage devices and loaded into memory of a computing device, such as server 304, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of the illustrative embodiments and is not a general purpose computing device. Moreover, as described herein, the implementation of the mechanisms of the illustrative embodiments improves the functionality of the computing device and provides a useful and concrete result that facilitates more accurate simulation in epidemiological computer models of the spread of an infectious disease in a population of interest by being able to adjust the models, in a pluggable fashion, for mobility isolation and use of countermeasures by the population of interest.

As shown in FIG. 3, in accordance with one illustrative embodiment, the various client computing devices 310 report their mobility information, through associated applications executing on these client computing devices 310, to the mobility and countermeasure data source(s) 190 of servers 306 and 308. The mobility and countermeasure data source(s) 190 gather this data from the client computing devices 310 and use this data to generate mobility and countermeasure data for the population 320, which his then reported to the MIC AI-ML engine 180 of the decision support AI system 330 executing on server 304. It should be appreciated that the mobility and countermeasure data source(s) 190 may further include, or obtain data from, other data reporting source computing systems, such as governmental organization computing systems, e.g., the CDC computing systems, state and/or federal health organization computing systems, or the like. Based on configuration information for the epidemiological computer model 100, the MIC AI-ML engine 180 deploys MIC compartments 332 into the epidemiological computer model 100 in association with specified compartments of the epidemiological computer model 100. The MIC AI-ML engine 180 further predicts isolation rates 334 based on the received mobility and countermeasure data from the source computing systems 190 and configures the connections between compartments and the MIC compartments in the epidemiological computer model 100 with the predicted isolation rate 334. The epidemiological computer model 100 is executed to generate state predictions for the infectious disease and the population 320 which are then used by the decision support AI system 330 to perform decision support operations in accordance with further AI logic of the decision support AI system 330. Results of the decision support operation may then be output to a client computing device 318 for use by a human user via a decision support interface 340.

As noted above, the mechanisms of the illustrative embodiments utilize specifically configured computing devices, or data processing systems, to perform the operations for augmenting compartmental epidemiological computer models with logic that controls flows between compartments in accordance with predictions of isolation rates based on mobility isolation and countermeasure use predictions. These computing devices, or data processing systems, may comprise various hardware elements which are specifically configured, either through hardware configuration, software configuration, or a combination of hardware and software configuration, to implement one or more of the systems/subsystems described herein. FIG. 4 is a block diagram of just one example data processing system in which aspects of the illustrative embodiments may be implemented. Data processing system 400 is an example of a computer, such as server 304 in FIG. 3, in which computer usable code or instructions implementing the processes and aspects of the illustrative embodiments of the present invention may be located and/or executed so as to achieve the operation, output, and external effects of the illustrative embodiments as described herein.

In the depicted example, data processing system 400 employs a hub architecture including north bridge and memory controller hub (NB/MCH) 402 and south bridge and input/output (I/O) controller hub (SB/ICH) 404. Processing unit 406, main memory 408, and graphics processor 410 are connected to NB/MCH 402. Graphics processor 410 may be connected to NB/MCH 402 through an accelerated graphics port (AGP).

In the depicted example, local area network (LAN) adapter 412 connects to SB/ICH 404. Audio adapter 416, keyboard and mouse adapter 420, modem 422, read only memory (ROM) 424, hard disk drive (HDD) 426, CD-ROM drive 430, universal serial bus (USB) ports and other communication ports 432, and PCI/PCIe devices 434 connect to SB/ICH 404 through bus 438 and bus 440. PCI/PCIe devices may include, for example, Ethernet adapters, add-in cards, and PC cards for notebook computers. PCI uses a card bus controller, while PCIe does not. ROM 424 may be, for example, a flash basic input/output system (BIOS).

HDD 426 and CD-ROM drive 430 connect to SB/ICH 404 through bus 440. HDD 426 and CD-ROM drive 430 may use, for example, an integrated drive electronics (IDE) or serial advanced technology attachment (SATA) interface. Super I/O (SIO) device 436 may be connected to SB/ICH 404.

An operating system runs on processing unit 406. The operating system coordinates and provides control of various components within the data processing system 400 in FIG. 4. As a client, the operating system may be a commercially available operating system such as Microsoft® Windows 10®. An object-oriented programming system, such as the Java™ programming system, may run in conjunction with the operating system and provides calls to the operating system from Java™ programs or applications executing on data processing system 400.

As a server, data processing system 400 may be, for example, an IBM eServer™ System p® computer system, Power™ processor based computer system, or the like, running the Advanced Interactive Executive (AIX®) operating system or the LINUX® operating system. Data processing system 400 may be a symmetric multiprocessor (SMP) system including a plurality of processors in processing unit 406. Alternatively, a single processor system may be employed.

Instructions for the operating system, the object-oriented programming system, and applications or programs are located on storage devices, such as HDD 426, and may be loaded into main memory 408 for execution by processing unit 406. The processes for illustrative embodiments of the present invention may be performed by processing unit 406 using computer usable program code, which may be located in a memory such as, for example, main memory 408, ROM 424, or in one or more peripheral devices 426 and 430, for example.

A bus system, such as bus 438 or bus 440 as shown in FIG. 4, may be comprised of one or more buses. Of course, the bus system may be implemented using any type of communication fabric or architecture that provides for a transfer of data between different components or devices attached to the fabric or architecture. A communication unit, such as modem 422 or network adapter 412 of FIG. 4, may include one or more devices used to transmit and receive data. A memory may be, for example, main memory 408, ROM 424, or a cache such as found in NB/MCH 402 in FIG. 4.

As mentioned above, in some illustrative embodiments the mechanisms of the illustrative embodiments may be implemented as application specific hardware, firmware, or the like, application software stored in a storage device, such as HDD 426 and loaded into memory, such as main memory 408, for executed by one or more hardware processors, such as processing unit 406, or the like. As such, the computing device shown in FIG. 4 becomes specifically configured to implement the mechanisms of the illustrative embodiments and specifically configured to perform the operations and generate the outputs described herein with regard to the MIC AI-ML engine and compartmental epidemiological computer model and/or the decision support AI computing system that employs the MIC AI-ML engine and compartmental epidemiological computer model.

Those of ordinary skill in the art will appreciate that the hardware in FIGS. 3 and 4 may vary depending on the implementation. Other internal hardware or peripheral devices, such as flash memory, equivalent non-volatile memory, or optical disk drives and the like, may be used in addition to or in place of the hardware depicted in FIGS. 3 and 4. Also, the processes of the illustrative embodiments may be applied to a multiprocessor data processing system, other than the SMP system mentioned previously, without departing from the spirit and scope of the present invention.

Moreover, the data processing system 400 may take the form of any of a number of different data processing systems including client computing devices, server computing devices, a tablet computer, laptop computer, telephone or other communication device, a personal digital assistant (PDA), or the like. In some illustrative examples, data processing system 400 may be a portable computing device that is configured with flash memory to provide non-volatile memory for storing operating system files and/or user-generated data, for example. Essentially, data processing system 400 may be any known or later developed data processing system without architectural limitation.

It should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc., which is executed by one or more processors of one or more computing devices that are then specifically configured to be specialized computing devices for implementing the mechanisms of the illustrative embodiments.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory coupled to the at least one processor and having instructions executed by the at least one processor to specifically configure the at least one processor to execute the method comprising:
    performing machine learning training of an isolation rate prediction AI computer model to generate a trained isolation rate prediction AI model that predicts an isolation rate of a biological population;
    receiving isolation data from one or more data source computing systems, wherein the isolation data comprises mobility data providing data indicating a measure of mobility of the biological population;
    executing the trained isolation rate prediction AI model on input features extracted from the isolation data to generate a predicted isolation rate;
    executing a compartmental epidemiological computer model comprising a plurality of compartments representing states of a population with regard to an infectious disease, to simulate a progression of the infectious disease; and
    controlling, during execution of the compartmental epidemiological computer model, a flow of portions of the monitored population from at least one first compartment to at least one second compartment in the compartmental epidemiological computer model based on the predicted isolation rate.

2. The method of claim 1, wherein controlling the flow of portions of the monitored population from at least one first compartment to at least one second compartment comprises:
    generating, in the compartmental epidemiological computer model, at least one mobility isolation and countermeasures (MIC) compartment in association with the at least one first compartment; and
    controlling a flow of a first portion of the monitored population into and out of the at least one MIC compartment based on the predicted isolation rate, wherein the MIC compartment represents a portion of the biological population that is isolated from other portions of the biological population.

3. The method of claim 1, wherein the mobility data is collected from a plurality of mobile computing devices associated with a plurality of individuals in the biological population, and wherein the mobility data is agnostic with regard to the infectious disease.

4. The method of claim 3, wherein the one or more data source computing systems comprises a location services computing system that collects the mobility data from the plurality of mobile computing devices.

5. The method of claim 4, wherein the mobility data is collected from mobile smartphones and analyzed by the trained isolation rate prediction AI computer model to determine a measure of how much members of the biological population interact with one another to determine a potential for spreading a disease modeled by the compartmental epidemiological computer model.

6. The method of claim 1, wherein the isolation data comprises countermeasure data obtained from at least one countermeasure source computing system that reports statistics of countermeasure use by the biological population.

7. The method of claim 6, wherein the countermeasures comprise data specifying governmental mandates applicable to a geographical region of the biological population.

8. The method of claim 1, further comprising:
    smoothening changes in the received isolation data over a predetermined period of time; and interpolating the isolation data to have continuous values; and executing the trained isolation rate prediction AI model on input features extracted from the isolation data to generate a predicted isolation rate comprises interpolating isolation rates for compartments of the compartmental epidemiological computer model based on results of interpolating the isolation data.

9. The method of claim 1, wherein the compartmental epidemiological computer model is a Susceptibility, Infected, and Recovered (SIR) based compartmental epidemiological computer model.

10. The method of claim 1, wherein a state of each compartment in the compartmental epidemiological computer model is output to an AI based decision support computing system that processes the state information to generate decision support outputs.

11. A computer program product comprising a non-transitory computer readable storage medium having a computer readable program stored therein, wherein the computer readable program, when executed in a data processing system, causes the data processing system to:

perform machine learning training of an isolation rate prediction AI computer model to generate a trained isolation rate prediction AI model that predicts an isolation rate of a biological population;

receive isolation data from one or more data source computing systems, wherein the isolation data comprises mobility data providing data indicating a measure of mobility of the biological population;

execute the trained isolation rate prediction AI model on input features extracted from the isolation data to generate a predicted isolation rate;

execute a compartmental epidemiological computer model comprising a plurality of compartments representing states of a population with regard to an infectious disease, to simulate a progression of the infectious disease; and control, during execution of the compartmental epidemiological computer model, a flow of portions of the monitored population from at least one first compartment to at least one second compartment in the compartmental epidemiological computer model based on the predicted isolation rate.

12. The computer program product of claim 11, wherein controlling the flow of portions of the monitored population from at least one first compartment to at least one second compartment comprises:

generating, in the compartmental epidemiological computer model, at least one mobility isolation and countermeasures (MIC) compartment in association with the at least one first compartment; and controlling a flow of a first portion of the monitored population into and out of the at least one MIC compartment based on the predicted isolation rate, wherein the MIC compartment represents a portion of the biological population that is isolated from other portions of the biological population.

13. The computer program product of claim 11, wherein the mobility data is collected from a plurality of mobile computing devices associated with a plurality of individuals in the biological population, and wherein the mobility data is agnostic with regard to the infectious disease.

14. The computer program product of claim 13, wherein the one or more data source computing systems comprises a location services computing system that collects the mobility data from the plurality of mobile computing devices.

15. The computer program product of claim 14, wherein the mobility data is collected from mobile smartphones and analyzed by the trained isolation rate prediction AI computer model to determine a measure of how much members of the biological population interact with one another to determine a potential for spreading a disease modeled by the compartmental epidemiological computer model.

16. The computer program product of claim 11, wherein the isolation data comprises countermeasure data obtained from at least one countermeasure source computing system that reports statistics of countermeasure use by the biological population.

17. The computer program product of claim 16, wherein the countermeasures comprise data specifying governmental mandates applicable to a geographical region of the biological population.

18. The computer program product of claim 11, further comprising:

smoothening changes in the received isolation data over a predetermined period of time; and interpolating the isolation data to have continuous values; and executing the trained isolation rate prediction AI model on input features extracted from the isolation data to generate a predicted isolation rate comprises interpolating isolation rates for compartments of the compartmental epidemiological computer model based on results of interpolating the isolation data.

19. The computer program product of claim 11, wherein the compartmental epidemiological computer model is a Susceptibility, Infected, and Recovered (SIR) based compartmental epidemiological computer model.

20. A data processing system, comprising:

at least one processor; and at least one memory coupled to the at least one processor, wherein the at least one memory comprises instructions which, when executed by the at least one processor, cause the at least one processor to:

perform machine learning training of an isolation rate prediction AI computer model to generate a trained isolation rate prediction AI model that predicts an isolation rate of a biological population;

receive isolation data from one or more data source computing systems, wherein the isolation data comprises mobility data providing data indicating a measure of mobility of the biological population;

execute the trained isolation rate prediction AI model on input features extracted from the isolation data to generate a predicted isolation rate;

execute a compartmental epidemiological computer model comprising a plurality of compartments representing states of a population with regard to an infectious disease, to simulate a progression of the infectious disease; and control, during execution of the compartmental epidemiological computer model, a flow of portions of the monitored population from at least one first compartment to at least one second compartment in the compartmental epidemiological computer model based on the predicted isolation rate.

* * * * *